(12) United States Patent
Rosenberg

(10) Patent No.: US 6,254,384 B1
(45) Date of Patent: Jul. 3, 2001

(54) CUSHIONED MOLAR GEAR FOR THE CORRECTION OF CLASS II AND CLASS III DENTAL MALOCCLUSIONS EMPLOYING IMPROVED COMPRESSION COUPLING MEANS

(76) Inventor: Farel Rosenberg, 9305 Beverly Crest Dr., Beverly Hills, CA (US) 90210

( * ) Notice: Subject to any disclaimer, the term of this patent is extended or adjusted under 35 U.S.C. 154(b) by 0 days.

(21) Appl. No.: 09/635,457

(22) Filed: Aug. 11, 2000

(51) Int. Cl.[7] ................................................. A61C 3/00
(52) U.S. Cl. ............................................................... 433/19
(58) Field of Search .................................. 433/18, 19, 21, 433/24

(56) References Cited

U.S. PATENT DOCUMENTS

| | | | |
|---|---|---|---|
| 4,472,139 | * | 9/1984 | Rosenberg ............................. 433/19 |
| 4,592,725 | * | 6/1986 | Goshgarian ............................. 433/7 |
| 4,708,646 | * | 11/1987 | Jasper ..................................... 433/19 |
| 5,246,366 | * | 9/1993 | Tracey .................................... 433/21 |
| 5,645,423 | * | 7/1997 | Collins, Jr. ............................. 433/21 |
| 5,678,990 | * | 10/1997 | Rosenberg ............................. 433/19 |
| 5,697,782 | * | 12/1997 | Klapper et al. ........................ 433/19 |
| 5,823,772 | * | 10/1998 | Vogt ....................................... 433/21 |
| 6,113,390 | * | 9/2000 | Sirney .................................... 433/19 |

* cited by examiner

Primary Examiner—Ralph A. Lewis
(74) Attorney, Agent, or Firm—Gilbert Kivenson

(57) ABSTRACT

A three part appliance for orthodontic and orthopedic cushioned correction of Class II and Class III dental malocclusions employing a simplified U shaped compression force module. The appliance allows a maximum amount of dental movement for the wearer in the horizontal and vertical planes, while exerting forward-backward corrective forces on the upper and lower dental arches and their supporting bone in their closed position.

3 Claims, 5 Drawing Sheets

CUSHIONED MOLAR GEAR FOR THE CORRECTION OF CLASS II AND CLASS III DENTAL MALOCCLUSIONS EMPLOYING IMPROVED COMPRESSION COUPLING MEANS

BACKGROUND OF THE INVENTION

This invention relates to improvements in my earlier three part interarch dental appliance entitled "Apparatus for Cushioned Bite Jumping and the Correction of Class II Malocclusions" which was patented on Oct. 21, 1997 (U.S. Pat No. 5,678,990). This device, by applying mechanical linkages and cylinders enclosing a force module to achieve the forward backward orthodontic-orthopedic forces between upper and lower teeth (and supporting bone), creates a normal bite. The teeth and bone structures are thus moved into proper orientation under controlled conditions. This apparatus, however, employs a relatively complex force mechanism between its parts. This force mechanism is expensive to manufacture and complex to assemble or replace when adjusting the appliance during treatment. In the present invention, a simplified U shaped compression force module has been substituted for the previous mechanism with no tubing or guide pins. Attachment to the rest of the apparatus is simple and carried out by means of two loosely riveted connections.

PRIOR ART

The present invention, like its predecessors, makes use of links and link housings. The housings are coupled to orthodontic upper and lower molar bands previously installed in the mouth by mounting pins which insert into corresponding mounting tubes attached to orthodontic molar bands by their mounting bases.

The links and link holders, attached to the upper and lower molars permit correction forces to be applied during closure of the mouth. In my earlier issued patents (U.S. Pat. Nos. 4,382,783 and 4,472,139) the upper and lower set of links were joined by adjustable, threaded members. These were inherently weak and tended to disengage or break under the transverse forces developed during mouth closure. In my last improvement (U.S. Pat. No. 5,678,990 cited above) the junction between the upper and lower links was accomplished by telescoping hollow cylinders, the inner cylinder containing a force element. The movement of the force element was guided by the inner surface of the smallest cylinder. The overall orientation of the cylinders was maintained by guide pins. Although this arrangement has proven satisfactory, it is still expensive to manufacture, complex and difficult to assemble.

SUMMARY OF THE INVENTION

The use of a simple external, "U" shaped compression force module permits a simplified approach that was not possible using the prior art. The force module flexes in a direction parallel to its mounting plane. The strength of the force module can be varied by changing its length, thickness, or altering the "rest width" of the open end of the "U" or its height or overall size.

In the present invention, the upper and lower sets of teeth are connected by this "U" shaped compression module, coupled by pivoted links to housings which in turn connect, by way of mounting pins, into their respective mounting tubes whose bases are attached to orthodontic molar bands placed on selected teeth in each side of the mouth. Additionally, the embedding of the mounting tube bases in appropriate molar areas of corresponding removable non-metallic upper and lower dental arch appliances and templates enhances its use. When the mouth is closing with the invention in place, the pivoted links act on the "U" shaped compression force module to redirect the closing forces into forward-backward force vectors. The invention makes use of this "U" shaped compression force module to transmit forces between the upper and lower teeth and their supporting bone. If a "light" force module is employed, the invention may be used to bring about orthodontic-tooth movement. With a "heavy" force module, orthopedic jaw displacement (as well as tooth movement) may be realized. The assembly of each molar gear unit is considerably simplified by this improvement and fabrication cost is lowered. If the position of the compression force module and the mounting components are reversed, the appliance will exert backward and downward forces on the lower teeth, and upward and forward forces on the upper teeth. This will produce forces during mouth closure which can be used in selected cases to treat class III protrusions.

DESCRIPTION OF THE FIGURES

In FIG. 1 are shown the link housings 7a and 7b, the links 8a and 8b, the loosely riveted connections, 12a, 12b, 12c, 12d, the mounting pins 6a and 6b and the mounting molar tubes, 14a and 14b into which the pins are inserted the metal mounting tube bases 15a and 15b, and the new U shaped compression force module (shown in relaxed mode at 9).

in FIGS. 7A–7D, it can be seen that the force applied at the left is not transmitted until the toggles U and L, approach and achieve full closure, 7C and 7D respectively. it is then that the U shaped compression force module is activated and the force transmitted.

DETAILED DESCRIPTION OF THE INVENTION

Figure 1:
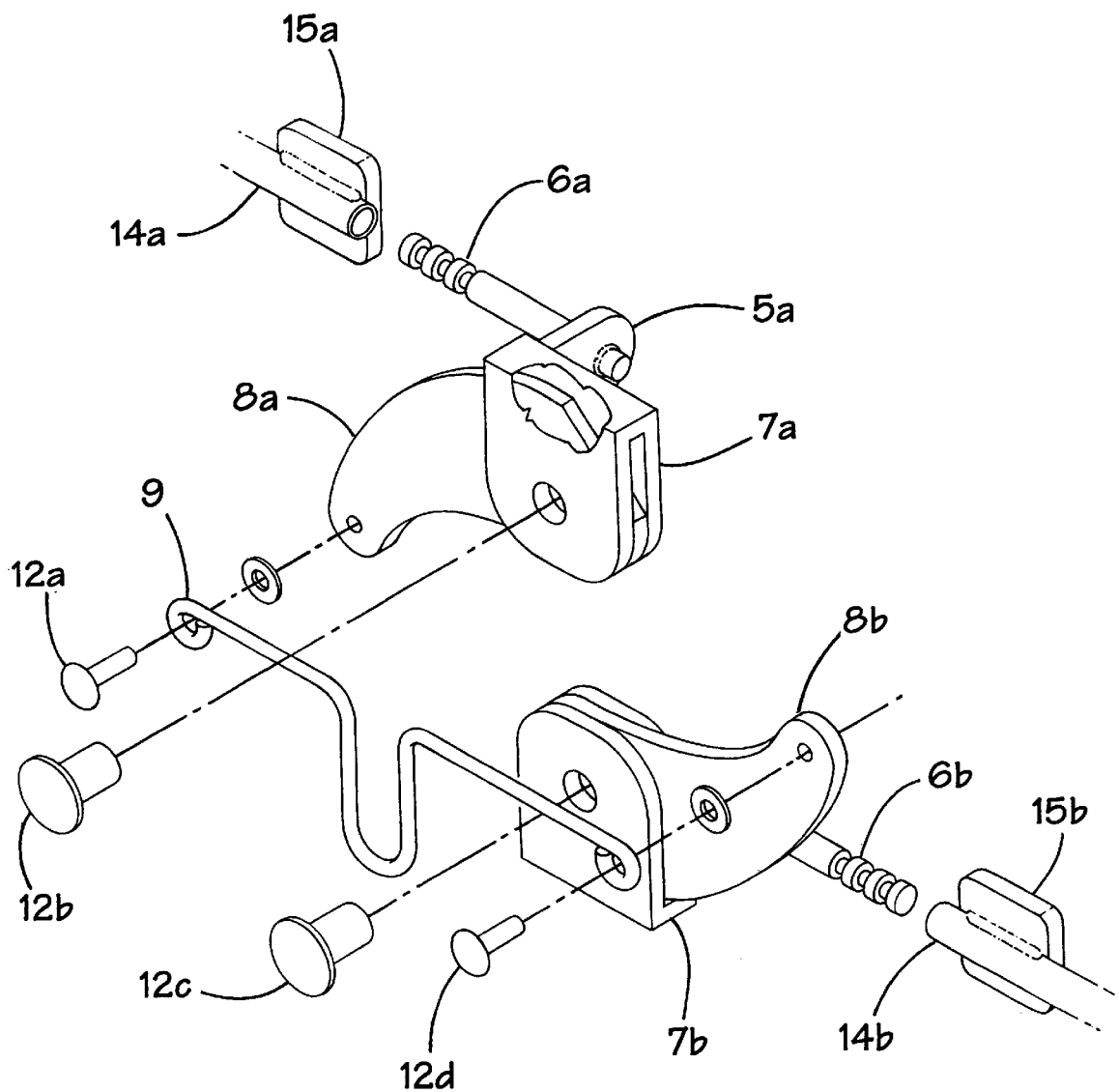
FIG. 1 is a perspective view of the appliance as configured to fit into the right side of the mouth.
Figure 2:
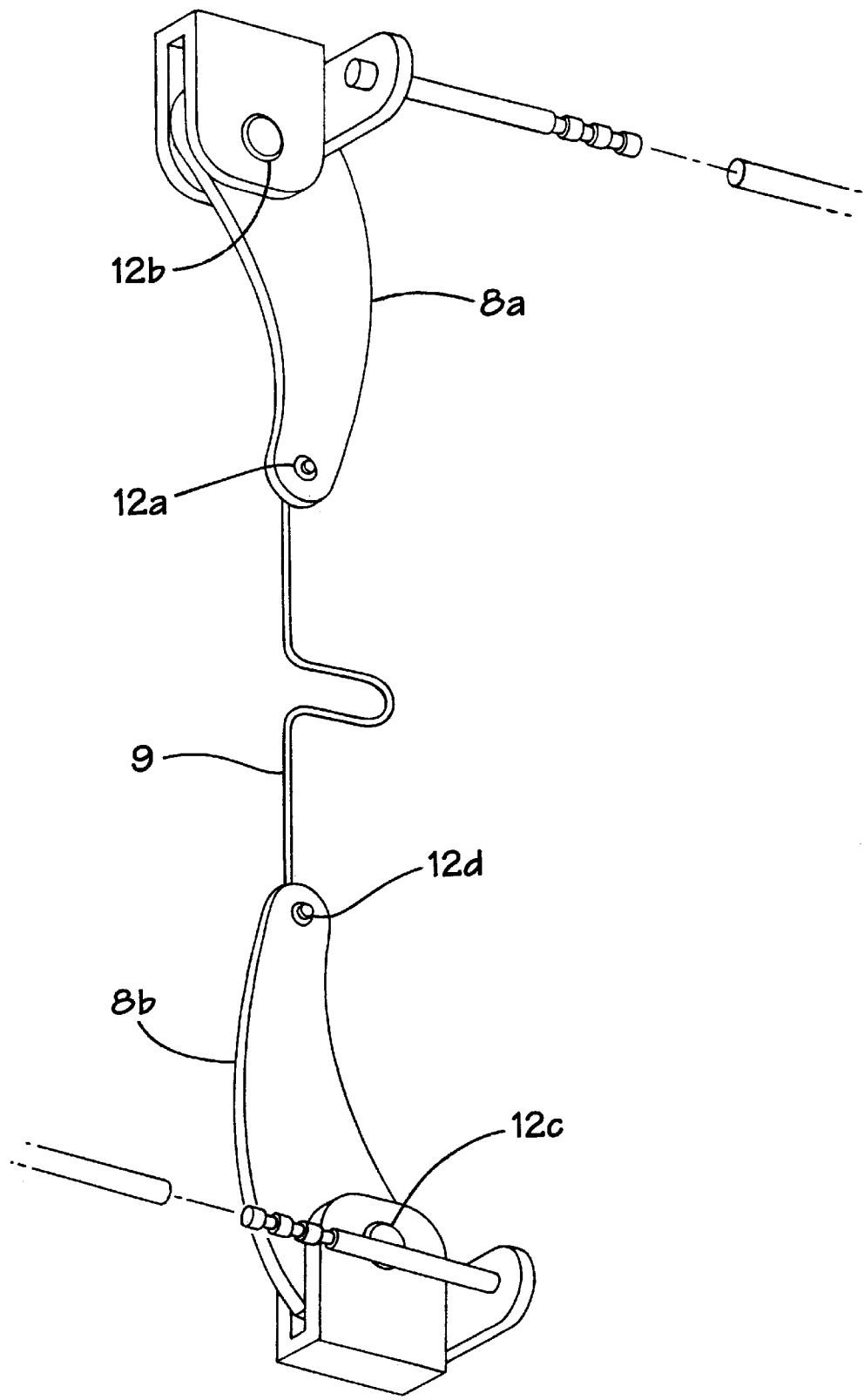
FIG. 2 is a perspective of the invention as mounted in the right side of the mouth with the jaws open. The links 8a and 8b are fully extended resulting from the rotatable loosely riveted connections 12a, 12b, 12c, 12d; the U shaped compression force module 9 is not activated.
Figure 4:
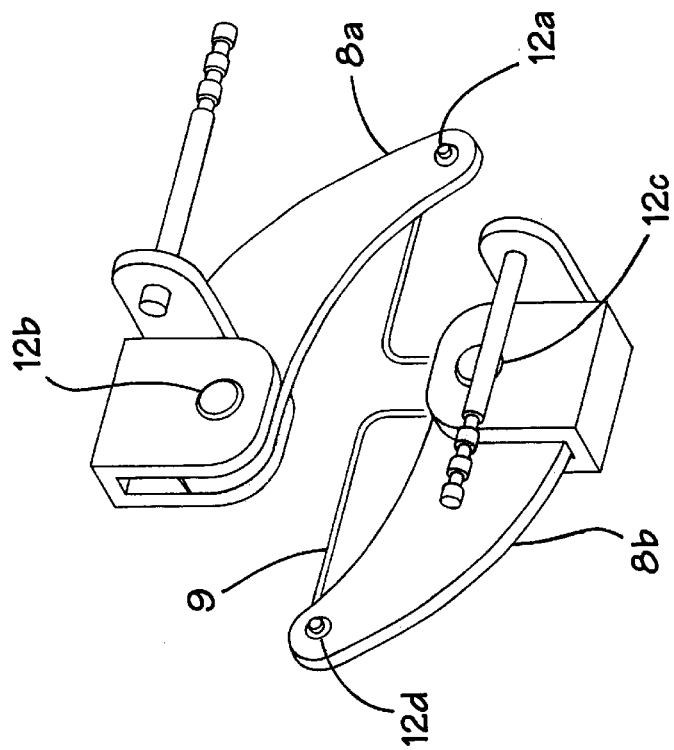
FIG. 4 is a perspective view of the invention shown in FIGS. 2 and 3 but with the mouth completely closed as allowed by link closure, again a result of the loosely riveted connections 12a, 12b, 12c, and 12d. The U shaped compression force module 9, however is now actively compressed and exerting orthodontic-orthopedic forces.
Figure 3:
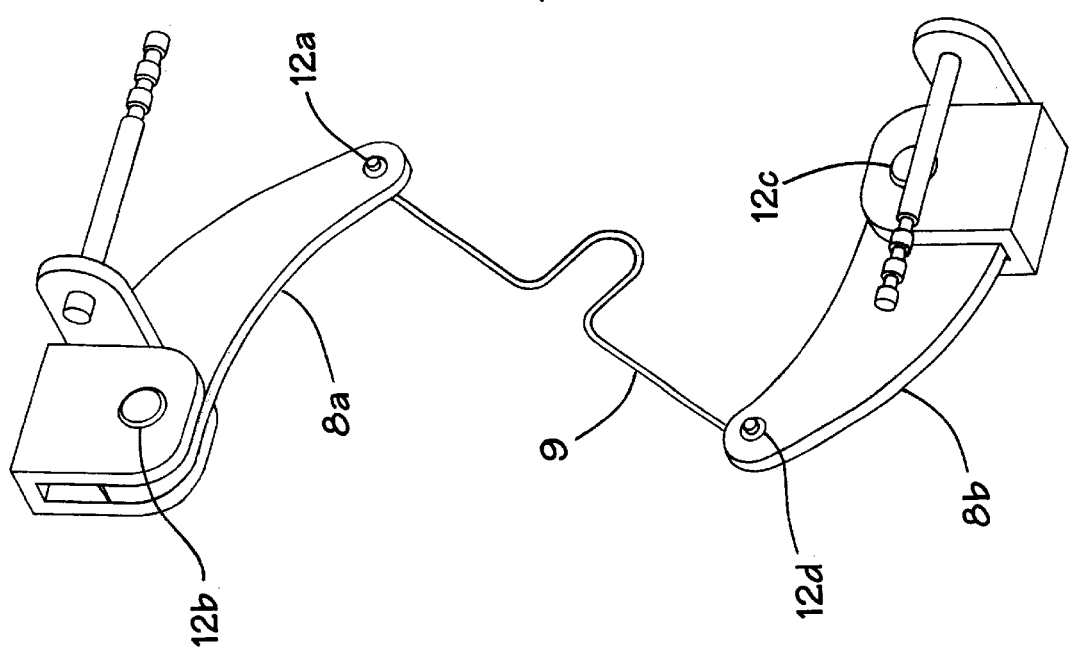
FIG. 3 is a perspective view of the invention as shown in FIG. 2 with the mouth partially closed. The U shaped force module 9 is still inactive.
Figure 5:
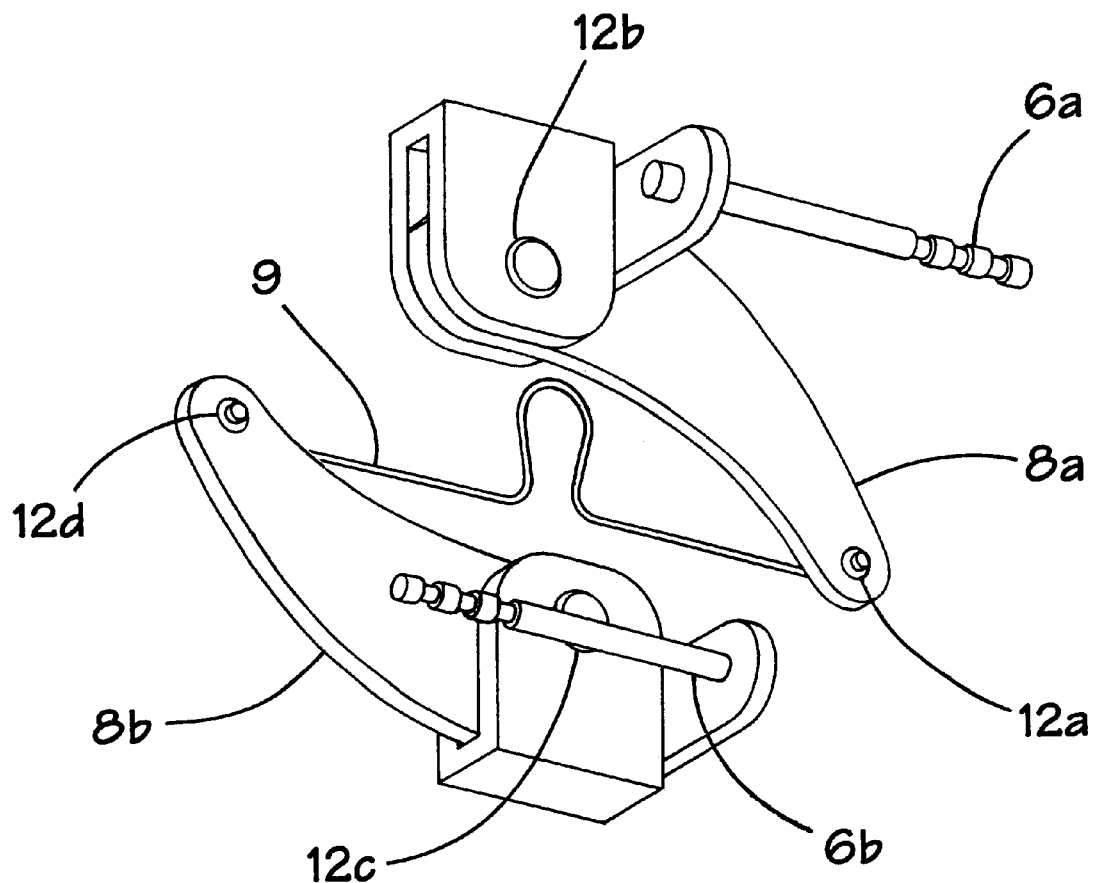
FIG. 5 shows a second embodiment of the "U" shape compression force module 9 in its active state. This version is inverted with the "U" pointing upward, and connected to the inner surface of its respective links 8a and 8b.

The component parts of the present invention, the molar gear, its functioning and the improvement to be gained by the use of a simple "U" shaped compression force module will be described with reference to FIGS. 1 to 4. The molar gear, FIG. 1 is sized and configured to fit into the right, left or both sides of the mouth between the upper and lower molars. The molar gear, FIG. 1 contains upper and lower links 8a and 8b rotatably mounted in upper and lower link housing 7a and 7b respectively. The link housings are rotatably mounted by pins 6a and 6b which fit into orthodontic mounting tubes 14a and 14b. The mounting tubes are attached to the respective mounting bases 15a and 15b which are either attached to molar orthodontic bands by soldering or embedded into the upper and lower molar areas of removable, non-metallic dental arch appliances and templates which are contributing to part of an orthodontic treatment program. The ends of links 8a and 8b are joined by the compression force module 9. A preferred method of fastening the links, link housings, and the compression force module in place is by loose riveting 12a, 12b, 12c, 12d. The plane of motion of the link housing is perpendicular to that of the links while the plane of motion of the compression force module is parallel to that of the links. In an earlier embodiment of my invention as shown and described in my patent U.S. Pat. No. 5,678,990, the upper and lower links were joined to two hollow, telescoping, tubes with guide pins, the inner of which containing a force element which served to confine the vertical motion of the links 8a and 8b into the respective housings 7a and 7b, as the mouth is closed. The assembly also served to transmit force from the upper to the lower teeth. The arrangement described above, although functioning very adequately, is complex and expensive to manufacture. The present invention eliminates telescoping tubing and guide pins and substitutes a U shaped compression force module 9 of varying lengths as needed, to couple the upper and lower links 8a and 8b. This coupling may be from either the cheek-outer or tooth-inner side of the respective links. The "U" portion of the compression module 9 may be pointed downward or upward. The inner attachment arrangement lessens cheek impingement of the appliance. The module has a low profile to protect it against occlusal interferences. The links 8a and 8b in turn protect said compression force module 9 from extension deformation through their opening, closing and rotational function—a result of the loosely riveted connections 12a, 12b, 12c, 12d of the links to their respective upper and lower housings 7a and 7b and to the compression force module 9. The compression force module 9 is inactive when the mouth is open but begins to compress when the links 8a and 8b approach and achieve a fully seated position in their respective housings 7a and 7b when the mouth is closed. This marks the onset point of inter-arch orthodontic-orthopedic correction, resulting in backward movement of the upper denture and forward movement of the lower, or the reverse, if used in the opposite Class III direction—a result of reciprocal forces. in addition to the above, the bases of the mounting tubes 15a and 15b to which are attached the mounting tubes 14a and 14b which receive the mounting pins 6a, and 6b of the appliance, may also be embedded In the required molar areas of corresponding removable non-metallic upper and lower dental arch appliances, to broaden usage. In the current preferred usage, the downward inclined "U" shaped compression force module "ends" are loosely riveted to the outer-cheek surface of the link ends 12a and 12d. This simple compression force module 9 by virtue of its shape confines upper and lower link 8a and 8b motion to a single plane. FIGS. 2–4 show this action as it would appear from the inside of the mouth. FIG. 2 shows the lower jaw at its wide-open position and the compression force module 9 is not active. In FIG. 3 the mouth is partially closed, and the compression force module 9 is still not active. In FIG. 4, the mouth is completely closed, and the compression force, module 9, is actively compressed and reciprocal forces are, being exerted on the lower and upper teeth. In FIG. 5, the "U" shaped compression force, module 9, is inverted and attached to the ends of the outer surface of the links 8a and 8b, adding protection to the module.

Figure 6:
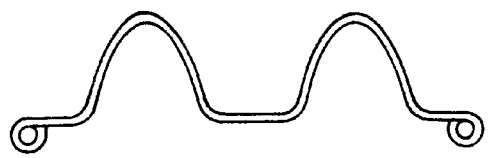
FIG. 6 shows a third embodiment of a compression force module. The latter is in the form of a double U shape, each half adjacent to the other. This rigid low profile configuration lends itself to orthopedic corrections. This variation lessens possible occlusal interferences.

FIG. 6 illustrates a second version of the compression force module. Here, because a lower profile double U is incorporated, a less flexible-orthopedic function is gained.

By varying the length and thickness of the entire compression force module, or specifically altering the U portion by adjusting the rest width of its open end, its height or its overall size, orthodontic and orthopedic force characteristics of the appliance are accomplished.

Figure 7:
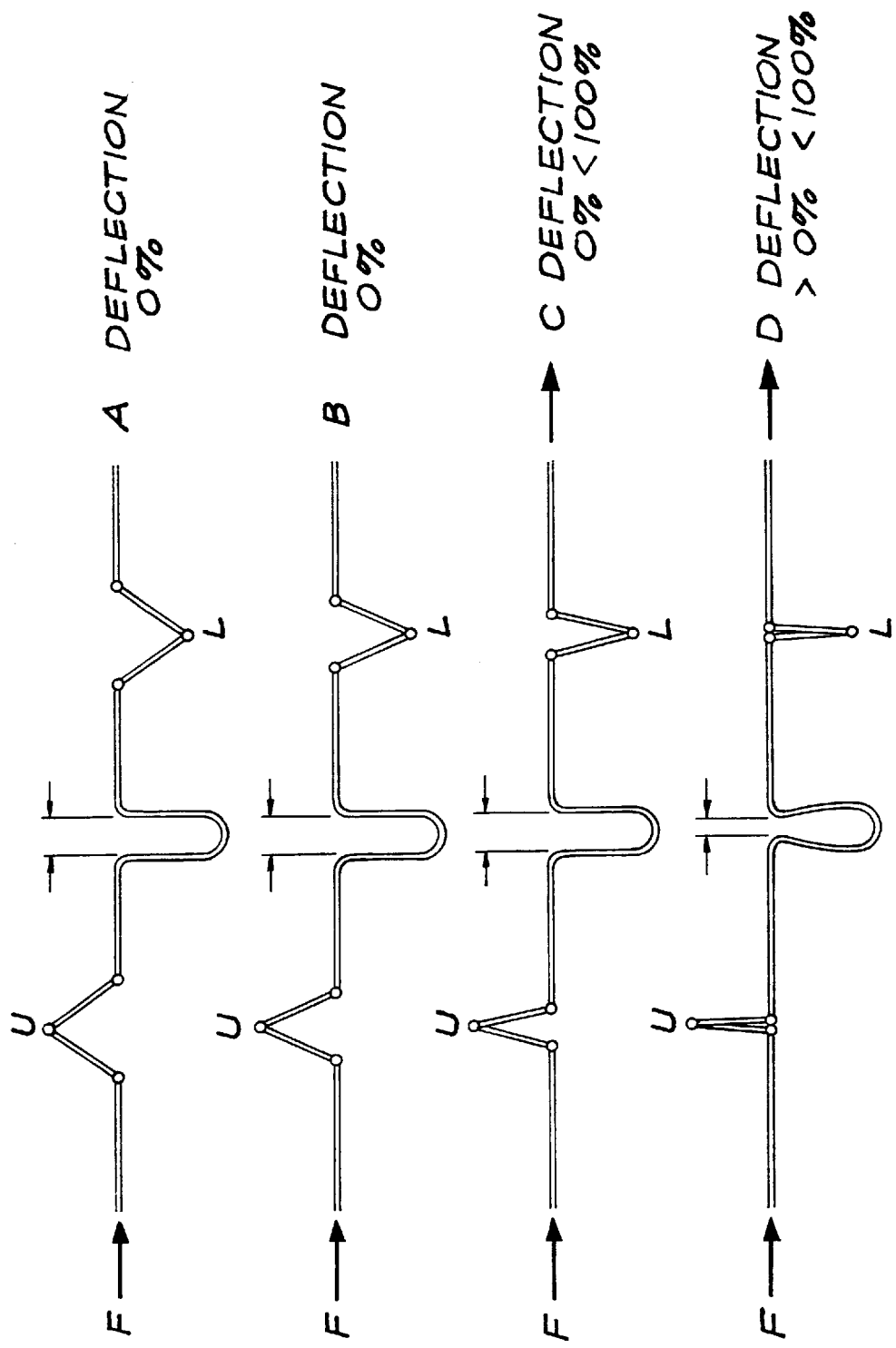
FIGS. 7A, 7B, 7C and 7D are schematic depictions of the actions of the invention as the mouth goes from fully opened to fully closed. The upper linkages are represented by the letter U; the lower linkage is represented by the letter L, both linkages are pictured as loosely joined toggle bars.

FIG. 7 represents the physics and the relationship of the links 8a and 8b, the housings 7a and 7b, and the compression force module 9, in producing orthodontic-orthopedic forces. The figure demonstrates the links 8a and 8b as loosely joined toggle bars U and L in the open position in FIGS. 7A and 7B. In approaching and achieving full closure in their respective housings 7a and 7b as the mouth closes U and L now reach the closed position, FIGS. 7C and 7D. It is then that the compression force module is activated and reciprocal forces transmitted.

These and other configurations may be utilized in carrying out the concept of the invention.

A variety of materials may be used in this construction. The compression force module may be constructed of metals and alloys such as stainless steel and nitinol, and non-metallic materials such as plastic, and quartz without departing from the concept of the invention.

What is claimed is:

1. A three part dental appliance for correcting orthodontic and orthopedic malocclusions by applying forces to selected molar teeth comprising
   a. an upper link housing assembly rotatably anchored to a molar in the upper dental arch;
   b. a lower link housing assembly rotatably attached to a selected molar in the lower jaw;
   c. a U-shaped force module flexibly joining said upper and lower link housing assemblies;
   d. an adjustable mechanical delay which requires a minimum closure to be reached before flexing force is exerted on said selected molar in the lower jaw;
   whereby, with separate appliances in place in the right and and left sides of the mouth, closure of the mouth overcomes the mechanical delay and then generates tooth and bone moving forces on said molars.

2. A three part dental appliance as described in claim 1 in which said rotatable anchors in the upper and lower link housings permit side to side movement without generating tooth moving forces, a patient comfort feature of the present invention.

3. A three part dental appliance as described in claim 1 in which the flexure of the U-shaped force module can be conveniently altered by changing the rest width, the height and wire diameter of the U so that treatment range variations can be accommodated.

* * * * *